United States Patent
Taubmann

(10) Patent No.: US 12,352,712 B2
(45) Date of Patent: Jul. 8, 2025

(54) METHOD AND SYSTEM FOR THE ANALYSIS OF BIOLOGICAL MATERIAL AND USE OF SUCH A SYSTEM

(71) Applicant: NETZSCH-Gerätebau GmbH, Selb (DE)

(72) Inventor: Rebekka Taubmann, Selb (DE)

(73) Assignee: NETZSCH-Gerätebau GmbH, Selb (DE)

( * ) Notice: Subject to any disclaimer, the term of this patent is extended or adjusted under 35 U.S.C. 154(b) by 0 days.

(21) Appl. No.: 18/633,790

(22) Filed: Apr. 12, 2024

(65) Prior Publication Data
US 2024/0264103 A1    Aug. 8, 2024

Related U.S. Application Data

(62) Division of application No. 17/231,601, filed on Apr. 15, 2021, now Pat. No. 12,222,304.

(30) Foreign Application Priority Data

May 8, 2020  (DE) ............... 10 2020 112 538.0

(51) Int. Cl.
| | | |
|---|---|---|
| *G01N 25/20* | (2006.01) | |
| *G01N 25/48* | (2006.01) | |
| *G01N 33/483* | (2006.01) | |
| *G16H 10/40* | (2018.01) | |
| *G16H 50/30* | (2018.01) | |

(52) U.S. Cl.
CPC ......... *G01N 25/20* (2013.01); *G01N 25/4866* (2013.01); *G01N 33/483* (2013.01); *G16H 10/40* (2018.01); *G16H 50/30* (2018.01)

(58) Field of Classification Search
CPC .. G01N 25/4866; G01N 33/483; G01N 25/20; G01N 333/48792; G16H 10/40; G16H 50/30; A61B 5/02; A61B 5/0022
See application file for complete search history.

(56) References Cited

U.S. PATENT DOCUMENTS

| | | | | |
|---|---|---|---|---|
| 2012/0274443 | A1* | 11/2012 | Kai ................ | A61B 5/14532 340/5.61 |
| 2018/0075222 | A1* | 3/2018 | Chen .............. | A61B 5/0015 |
| 2019/0003995 | A1 | 1/2019 | Monaselidze et al. | |
| 2021/0231593 | A1* | 7/2021 | Joo ................ | G01N 33/574 |

FOREIGN PATENT DOCUMENTS

WO    2017066800 A1    4/2017

* cited by examiner

*Primary Examiner* — Mirellys Jagan
(74) *Attorney, Agent, or Firm* — Whitmyer IP Group LLC

(57) ABSTRACT

A method for the analysis, in particular for analysis by dynamic difference calorimetry (DSC), of biological material, in particular blood, urine, sweat or skin tissue, with the steps of: introduction of a sample with a patient's biological material onto a sensor of a measuring device; acquisition of measured values by means of the measuring device; sending the measured values to an evaluation device, which communicates with the measuring device; assessment of the patient's state of health with the aid of data structures characterizing the state of health on the basis of the measured values by means of the evaluation device, on which a first application software instance is performed; and visualization or audio-visualization of the state of health on a display. The present invention further creates a system for the analysis of biological material and a use of such a system.

20 Claims, 4 Drawing Sheets

METHOD AND SYSTEM FOR THE ANALYSIS OF BIOLOGICAL MATERIAL AND USE OF SUCH A SYSTEM

TECHNICAL FIELD

The present invention relates to a method and a system for the analysis, in particular for analysis by dynamic difference calorimetry (DSC), of biological material, in particular blood, urine, sweat or skin tissue, as well as a use of such a system.

BACKGROUND

Analyses for detecting illnesses by means of dynamic difference calorimetry (DSC) are typically used in the medical sector in research. The design of the required measurement equipment chiefly includes equipment which is common and can be used in research laboratories. Consequently, some components, for example measuring devices and power supply, are designed immobile, since they are connected for example via a power cable to a power supply of the building. In addition, the cost of measurement equipment is at a level which institutions outside research and private individuals are unable to afford and they therefore forgo acquisition. As a result, waiting times for required analyses in particular are very long and the capacities for analyses are very small per unit of time.

Furthermore, investigations from research laboratories show that illnesses can be detected, and the courses of illnesses can be monitored with the aid of analyses by means of dynamic difference calorimetry. Such analyses, compared to conventional blood analyses such as can alternatively be carried out, offer very much more detailed information about the state of health of a patient.

Devices and methods are known such as are typically used for research purposes.

US 2019/0003995 A1 describes a dynamic difference calorimeter device for detecting illnesses and monitoring the therapeutic efficacy by detecting heat-resistant variants of proteins and/or metabolism products in biological samples.

WO 2017/066800 A1 describes methods for characterizing and/or predicting risks associated with a biological sample using thermal stability profiles.

It is the problem of the present invention to create possibilities for more cost-effective, simpler, and quicker detection of illnesses.

SUMMARY

According to the invention, this problem is solved in each case by the subject-matter of the independent claims.

According to a first aspect of the invention, a method is provided for the analysis, in particular for analysis by dynamic difference calorimetry (DSC), of biological material, in particular blood, urine, sweat or skin tissue. The method comprises the steps of introducing a sample with a patient's biological material onto a sensor of a measuring device and acquiring measured values by means of the measuring device. Furthermore, the method comprises the steps of sending the measured values to an evaluation device, which communicates with the measuring device, assessing the patient's state of health with the aid of data structures characterizing the state of health on the basis of the measured values by means of the evaluation device, on which a first application software instance is performed, as well as visualization or audio-visualization of the state of health on a display.

According to a second aspect of the invention, a system is provided for the analysis, in particular for analysis by dynamic difference calorimetry (DSC), of biological material, in particular blood, urine, sweat or skin tissue. The system comprises a measuring device, which comprises a sensor which contains a sample with a patient's biological material, and which is designed to send measured values to an evaluation device. Furthermore, the system comprises an evaluation device which comprises a first application software instance and is designed to receive the measured values and to assess the patient's state of health with the aid of data structures characterizing the state of health on the basis of the measured values. Furthermore, the system comprises a display, which is designed to visualize or audio-visualize the state of health.

According to a third aspect of the invention, a use of a system according to the invention for the analysis of biological material is provided.

An idea underlying the present invention consists in being able to quickly detect the state of health of patients and to monitor the courses of the states of health in a detailed manner. The invention can serve both as an additional aid for doctors as well as an independent instrument for monitoring the day-to-day state of health of private individuals. Since it is intended in particular for persons who are not specially trained to have their state of health assessed without a long waiting time and at an acceptable cost, the system proposed here is designed as a mobile system. Furthermore, the system or the components of the system can also be compatible with and/or connected to other communication-enabled objects, so that the system or the components of the system can for example be carried on the body.

Advantageous embodiments and developments emerge from the sub-claims related back to the independent claims and from the description with reference to the figures.

According to an embodiment of the method, datasets with medical information are taken into account in addition to the measured values when the state of health is assessed. On the basis of comprehensive datasets from other sources, which go beyond the measured data of the primary method, the state of health can thus be assessed more precisely. Relevant datasets could be past medical information on the patient and/or data from other measurement methods, which the patient uses in addition to the present method.

According to a development, the datasets comprise comparable measured values of other patients and/or treatment measures applied to the comparable measured values, and the datasets are transmitted to the evaluation device by communicative coupling of the evaluation device with a data-processing device. States of health validated by doctors or other trained personnel, which are based on comparable measured values of other patients, thus assist in obtaining more reliable information during the assessment of the state of health. Furthermore, treatment measures can be recommended in a targeted manner since the latter have already been successfully used for example with comparable measured values.

According to a further development, the datasets comprise vital parameters of the patient, in particular blood sugar level, blood pressure, heart rate and suchlike, which are transmitted to the evaluation device by communicative coupling of the evaluation device with diagnostic devices, in particular blood sugar/blood pressure measuring devices or suchlike, and/or computer hardware, in particular fitness trackers, wherein the vital parameters are taken essentially at the same time as the sample with biological material. For the assessment of the state of health, use can thus be made of datasets which can be taken independently by persons not specially trained, usually by means of devices easy to operate, and consequently enable a better overall assessment of the patient's state of health. The evaluation device can be fed with datasets either continuously or by a respective release at the corresponding devices.

According to a further embodiment of the method, the measuring device performs a thermal analysis process for measuring a released or absorbed amount of heat of the biological material during a thermal process. The state of health of the patient can be assessed more precisely by the analysis of biological material as a function of temperature since the thermal analysis is more detailed and therefore more informative than the standard blood analysis.

According to a further embodiment, the measuring device or the sensor is disposed of after the assessment step. In this way, necessary hygiene guidelines can be complied with and errors due to the assessment of the state of health by contaminated sensors or measuring devices can be reduced, since the sensor or the measuring device is always new and for example separately packaged for each application and the protective packaging is not removed until the sensor or the measuring device is used.

According to a further embodiment, the evaluation device communicates with a device which is preferably constituted as a mirror, a television and/or computer hardware, in particular PC, smart phone, smart watch and/or fitness tracker, via respective communication interfaces. The evaluation device can thus retrieve from the device or transmit thereto datasets, in particular data memories available on the patient, such as a cloud or suchlike, or datasets stored on servers of clinics or hospitals, without itself being coupled communicatively with a server or suchlike. The patient's personal data can thus be more easily protected.

According to a development, a second application software instance stored on the device or on a server is performed during the assessment of the state of health, which enables a more precise assessment of the state of health than the first application software instance of the evaluation device, and/or the state of health is visualized or audio-visualized on a display of the device. By means of the second application software instance, the application complexity and the information output can be increased compared to the first application instance, so that trained personnel, such as doctors for example, additionally receive in a displayed form the measured values measured in the measuring device and, on the basis thereof, can validate the state of health assessed by the evaluation device or receive in a displayed form a more comprehensive assessment of the state of health than untrained personnel, who receive in a displayed form a less differentiated assessment of the state of health on the basis of the measured values which can scarcely be interpreted by them.

According to a further embodiment, the method also includes a step for controlling the communication-enabled equipment in the building, in particular heating systems, building ventilation systems and/or alarms, in order to support treatment measures for the patient depending on the assessed state of health. The immediate surroundings of the patient, in particular the room temperature, air humidity and/or brightness can thus automatically be adapted to recommended treatment measures. Furthermore, by means of equipment in the building, reminders, or information, for example for upcoming medication times, can be transmitted visually and/or acoustically to the patient.

According to an embodiment of the system, the evaluation device also comprises a communication interface, which is designed to establish a communication connection between the evaluation device and an external communication participant and to transmit datasets with medical information from the external communication participant to the evaluation device for the assessment of the state of health. The evaluation device is thus capable of assessing still more precisely the state of health on the basis of additional datasets from the external communication participant, which go beyond the measured data of the primary method. Additional datasets could be past medical information about the patient and/or data from other measurement methods, which the patient uses in addition to the present method.

According to a development of the system, the external communication participant is constituted as a data-processing device and is coupled communicatively with the evaluation device via the communication interface, wherein the datasets include in particular comparable measured values of other patients and/or treatment measures applied to comparable measured values. States of health validated by doctors or other trained personnel and stored on the data-processing device, which are based on comparable measured values of other patients, can be available to the evaluation device in order to obtain more reliable information. Furthermore, treatment measures can be presented on the display in a targeted manner since the latter have already been successfully used for example with comparable measured values.

According to a further development of the system, the external communication participant is constituted as a diagnostic device, in particular as a blood sugar/blood pressure measuring device or suchlike, and/or as computer hardware, in particular as a fitness tracker, and is communicatively coupled with the evaluation device via the communication interface, wherein the datasets preferably comprise vital parameters of the patient, in particular blood sugar level, blood pressure, heart rate and suchlike. For the assessment of the state of health, datasets can be used for the evaluation device which can be acquired independently by persons not specially trained, usually by means of devices easy to operate, and consequently a better overall assessment of the patient's state of health is enabled. The evaluation device can be fed with datasets either continuously or by the respective release to the corresponding devices.

According to a further embodiment of the system, the measuring device is also designed to enable a thermal analysis process for measuring a released or absorbed amount of heat of the biological material during a thermal process. By the fact of the measuring device is capable of enabling the analysis of biological material as a function of temperature, the state of health of the patient can be assessed more precisely, since the thermal analysis is more detailed and therefore more informative than a standard blood analysis.

According to a further embodiment of the system, the measuring device or the sensor is a disposable product. In this way, necessary hygiene guidelines can be complied with and errors due to the assessment of the state of health by contaminated sensors or measuring devices can be reduced, since the sensor or the measuring device is always new and for example separately packaged for each application and the protective packaging is not removed until the sensor or the measuring device is used.

According to a development of the system, the external communication participant is preferably constituted as a mirror, a television, a server and/or computer hardware, in particular PC, smart phone, smart watch and/or fitness tracker, for the visualization or audio-visualization of the state of health. The evaluation device is thus designed to retrieve from or transmit to the external communication participant datasets stored in particular on servers of clinics or hospitals, without itself being coupled communicatively with a server or suchlike. The patient's personal data can thus be more easily protected.

According to a further development of the system, the external communication participant or a server coupled via the communication interface comprises a second application software instance, which enables a more precise assessment of the state of health than the first application software instance. The first application software instance can thus be set up with regard to application complexity and information output according to the specialist knowledge to be expected of the user. By means of the second application software instance, the application complexity and the information output can be increased compared to the first application software instance, so that measured values can also be displayed for trained personnel, such as doctors for example, and on the basis thereof the assessed state of health can be validated or a more comprehensive assessment of the state of health is displayed than for untrained personnel, who are capable of a less differentiated assessment of the state of health on the basis of the measured values which can scarcely be interpreted by them.

According to a further embodiment of the system, the measuring device, the evaluation device, and the display are at least partially surrounded by a housing, in particular a common housing. The system or at least components of the system are thus constituted mobile and portable.

The above embodiments and developments can, insofar as reasonable, be combined with one another arbitrarily. Further possible embodiments, developments and implementations of the invention also include combinations not explicitly mentioned of features of the invention described above or in the following with respect to the examples of embodiment. In particular, the specialist will also add individual aspects as improvements or supplements to the given basic form of the present invention.

BRIEF DESCRIPTION OF THE DRAWINGS

The present invention is explained in greater detail below with the aid of examples of embodiments making reference to the appended figures of the drawings. In the figures.

DETAILED DESCRIPTION

Figure 1:
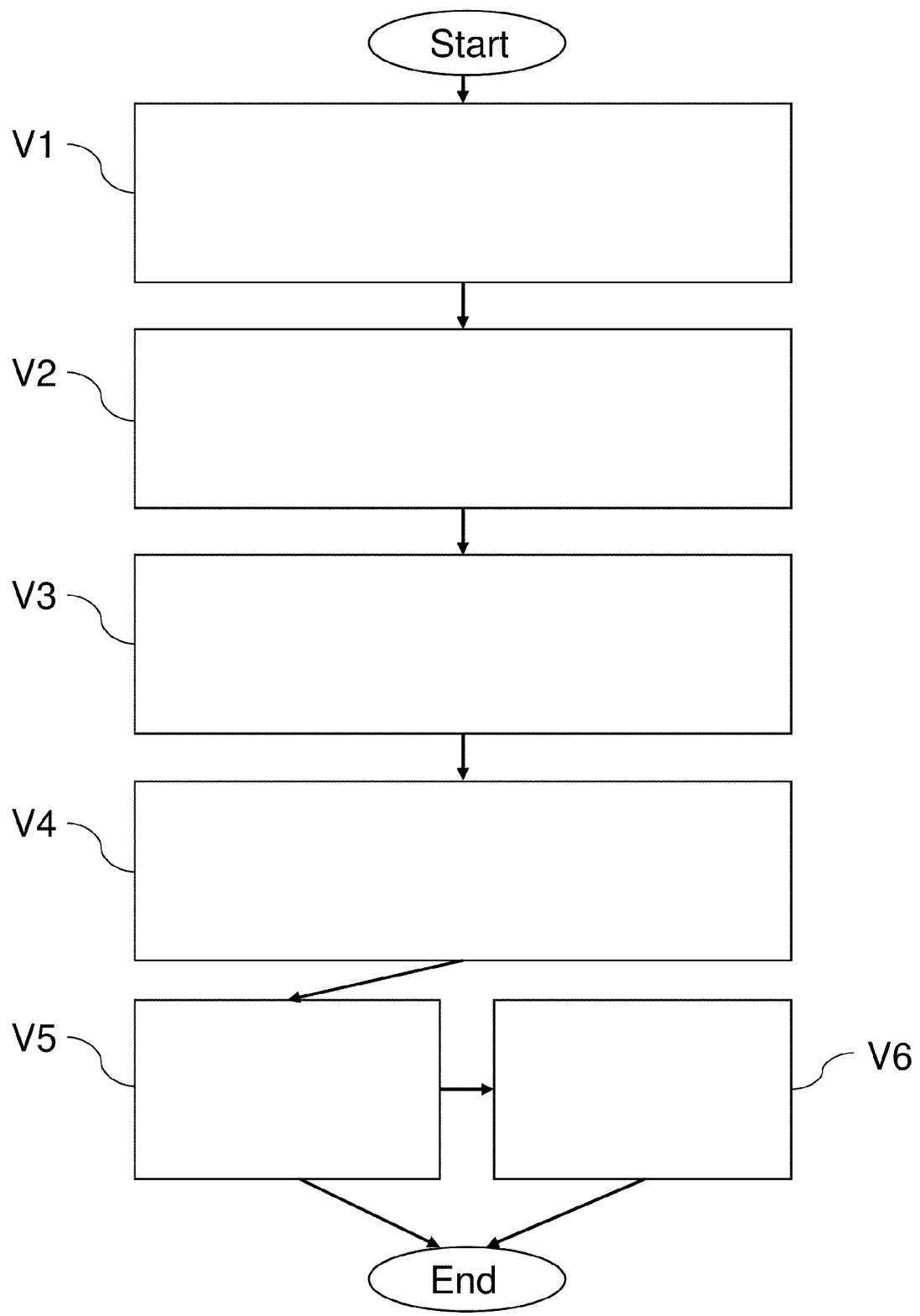
FIG. 1 shows a flow chart of a method for the analysis, in particular for analysis by dynamic difference calorimetry (DSC), of biological material, in particular blood, urine, sweat or skin tissue, according to an example of embodiment of the invention.

In the figures of the drawing, identical elements, features, and components having the same function or the same action—unless stated otherwise—are each provided with the same reference numbers.

Although specific embodiments and developments are represented and described here, it will be preferable for the specialist that a multiplicity of alternative and/or similar embodiments can replace the represented and described specific examples of embodiment, without departing from the scope of the present invention. This application is generally intended to cover all modifications or amendments to the specific examples of embodiment described herein.

The appended figures are intended to provide a further understanding of embodiments of the invention and, in combination with the description, serve to explain principles and concepts of the invention. Other examples of embodiment and many of the stated advantages emerge with regard to the drawings. The drawings are to be understood solely as diagrammatic drawings and the elements of the drawings are not necessarily represented true to scale with respect to one another. Direction-indicating terminology such as for example "above", "below", "left-hand", "right-hand", "over", "under", "horizontal", "vertical", "front", "rear" and similar indications are used solely for the purpose of explanation and do not serve to limit the generality to specific embodiments as shown in the figures.

Dashed lines on the figures of the drawings illustrate that the connections between the components connecting the dashed lines do not necessarily have to have physical contact with one another but can as it were be coupled together wireless.

FIG. 1 shows a flow chart of a method for the analysis, in particular for analysis by dynamic difference calorimetry (DSC), of biological material, in particular blood, urine, sweat or skin tissue of animal or human origin, according to an example of embodiment of the invention. The method contains the steps of introduction V1 of a sample 4, acquisition V2 of measured values, sending V3 the measured values to an evaluation device 5, assessment V4 of a patient's state of health and visualization or audio-visualization V5 of the state of health.

The introduction V1 of a sample 4 with biological material of the patient onto a sensor 3 of a measuring device 2 can be carried out in a number of possible ways. The biological material can be introduced onto sensor 3 by the biological material being introduced directly onto sensor 3 or into a container 14, for example a crucible or suchlike, wherein container 14 makes contact with sensor 3 or is contained in sensor 3.

For example, the patient's blood, as a biological material, which has been extracted from the patient by means of a lancet or a similar puncturing device, can be deposited on a chip, into container 14 or directly onto sensor 3. It is also conceivable that the puncturing device extracts blood automatically by release from the patient or at predefined intervals, so that the latter can be introduced onto sensor 3. Furthermore, sample 4 can be the patient's urine and introduced by means of a pipette, in particular a disposable pipette, onto sensor 3. Furthermore, sweat or skin tissue for example can be introduced as a biological material using suitable handling means or otherwise. Alternatively, the biological material can be introduced passively onto sensor 3, for example through provided openings/channels, which place the biological material structurally by gravity onto sensor 3. The selection of the biological material for analysis is not limited to the stated examples, but can comprise further biological materials, which enable medically useful information to be provided concerning the state of health of the patient.

The measured values are acquired V2 in measuring device 2. For this purpose, measuring device 2 can preferably carry out a thermal analysis process for measuring a released or absorbed amount of heat of the biological material during a thermal process. This thermal analysis procedure can be carried out in particular as dynamic difference calorimetry. Moreover, use can also be made of thermogravimetry or a simultaneous thermal analysis, as a result of which a measurement of the loss of mass of sample 4 and/or infrared spectroscopy of gases arising due to the heating of sample 4 is possible. Furthermore, use can also be made of other methods of analysis known in the medical sector. Irrespective of the method of analysis used, the measured values can also comprise measured values of a known reference 13, wherein reference 13 passes through the method of analysis in parallel with sample 4 and thus serves as a comparison.

Irrespective of the method of analysis used, the measured values can also comprise measured values of a known reference 13, wherein reference 13 passes through the method of analysis in parallel with sample 4 and thus serves as a comparison.

In the step of sending V3 the measured values to evaluation device 5, which communicates with measuring device 2, the communication can be implemented both wireless, for example by means of Bluetooth or WLAN, as well as wire-bound, for example by means of LAN or USB. Evaluation device 5 and measuring device 2 can communicate either directly through corresponding communication interfaces or via a data-processing device, in particular a PC, a smart phone or comparable digital communication devices. The form of communication between measuring device 2 and the possible data-processing device as well as between the possible data-processing device and evaluation device 5 does not have to be identical. Furthermore, evaluation device 5 can communicate via respective communication interfaces with a device which is preferably constituted as a mirror, a television and/or computer hardware, in particular PC, smart phone, smart watch and/or fitness tracker.

In a further step V4, the patient's state of health is assessed with the aid of data structures characterizing the state of health on the basis of the measured values by means of evaluation device 5, on which a first application software instance 6a is performed. The data structures characterizing the state of health can be specific data points, which are recorded for example during the dynamic difference calorimetry. Sample 4 and reference 13, which are both analyzed in an essentially identical container 14, for example a crucible, or on essentially identical sensors 3, experience the same thermal effect due to temperature-control elements 12.

Due to the thermal capacity of sample 4 or reference 13 and exothermal or endothermal processes, such as for example melting or evaporation, temperature differences and therefore different measured values for the same measured variable can occur between sample 4 and reference 13. Depending on the time at which differences between sample 4 and reference 13 occur in the analysis process and depending on how large these differences turn out to be, data structures arise which are regarded as characteristic of a specific state of health.

Furthermore, during assessment V4 of the state of health, a second application software instance 6b stored on the device or on a server can be performed, which enables a more precise assessment of the state of health than first application software instance 6a of evaluation device 5. Alternatively, or in addition, the state of the health can be visualized or audio-visualized on a display of the device.

The configuration of application software instances 6a, 6b can be differentiated for example over four configuration levels. Output possibilities of application software instances 6a, 6b are adapted to the user target groups to be expected, in particular to their medical knowledge to be assumed. For example, four user target groups are mentioned, private individuals without medical knowledge, chemists, family doctors and consultants, hospitals and other medical laboratory institutions, the medical knowledge of which increases in the sequence in which they are named. On the basis of the four configuration levels, for the given user target group the assessed state of health of the patient that is understandable to it can be visualized or audio-visualized. It is thus possible to introduce sample 4 into measuring device 2 independently, for example at home, and to transmit the measured values to an expert, such as a doctor for example, in the distance, in order to use his more comprehensive output possibilities of second application software instance 6b, which is stored for example on his server in the doctor's practice, and to use his specialist assessment in respect of the visualized state of health.

Optionally, measuring device 2 and/or sensor 3 can be disposed of after the step of assessment V4. A step of cleaning measuring device 2 or sensor 3 is thus unnecessary since sensor 3 or measuring device 2 is always new and for example separately packaged for each application and the protective packaging is not removed until sensor 3 or measuring device 2 is used.

Furthermore, the method comprises a visualization or audio-visualization V5 of the assessed state of health and of the course of the state of health over a specific past period of time on a display 7. The required information can be transmitted wire-bound or wireless from the evaluation device to display 7.

Moreover, the measured values and/or the assessed state of health can be stored locally on a data medium or on a server, in particular in a cloud. Moreover, the measured values and/or the assessed state of health can be exchanged with doctors, clinics, chemists, hospitals, manufacturers of the devices which carry out the method according to the invention, and/or other devices which carry out the method according to the invention.

Furthermore, the method can comprise a step of controlling V6 communication-enabled installations in the building, for example heating systems, ventilation systems in the building and/or alarms, in order to support treatment measures for the patient depending on the assessed state of health.

Figure 2:
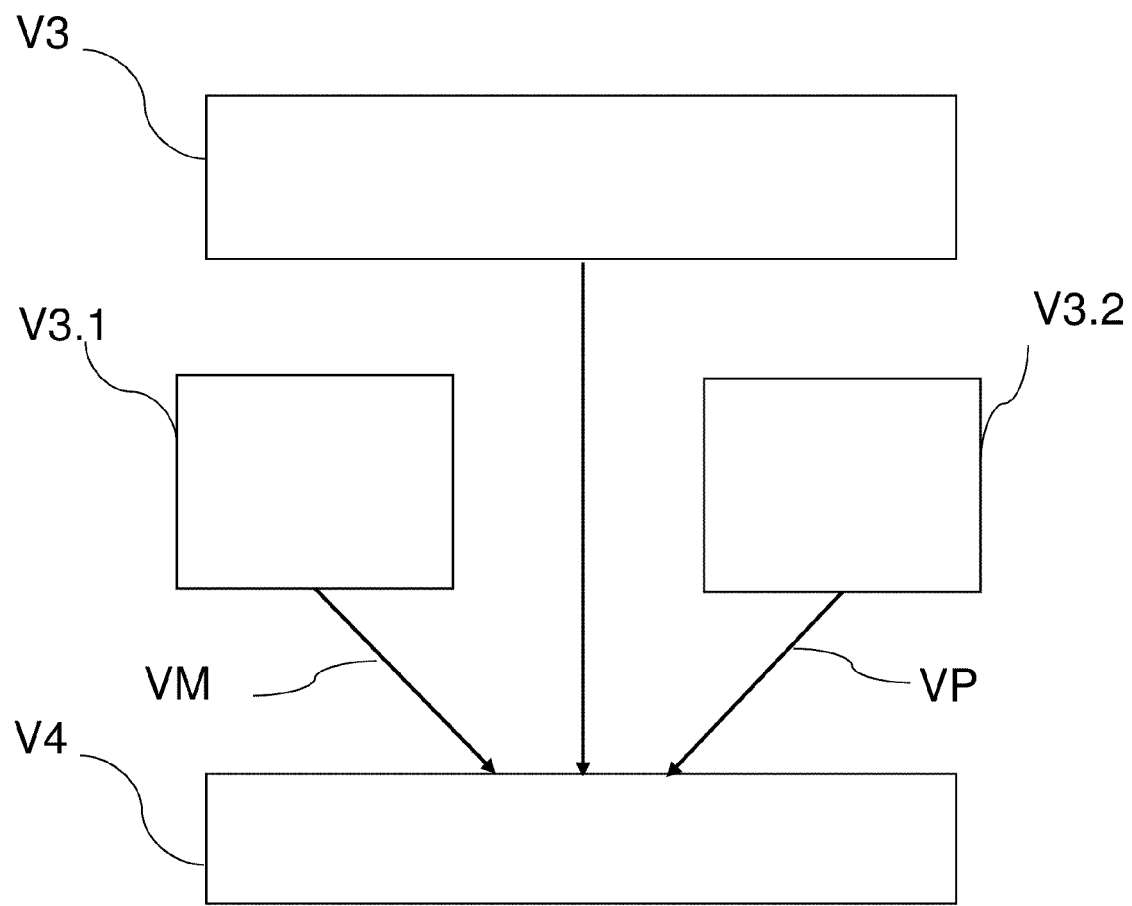
FIG. 2 shows a detail of a flow chart for a further example of embodiment of the steps of sending the measured values and assessing the state of health of the method according to the example of embodiment according to FIG. 1.

FIG. 2 shows a detail of a flow chart for a further example of embodiment of the steps of sending V3 the measured values and evaluation V4 of the state of health of the method according to the example of embodiment according to FIG. 1.

In the example of embodiment according to FIG. 2, datasets with medical information are taken into account in assessment V4 of the state of health in addition to the measured values which are provided by measuring device 2, in order to provide the greatest possible number of reference points for the characterizing data structures. These datasets can comprise medical information from at least two different areas. On the one hand, the datasets can comprise comparable measured values VM of other patients and/or treatment measures applied to comparable measured values. The datasets can be transmitted to evaluation device 5 by communicative coupling V3.1 of evaluation device 5 with a data-processing device, in particular a PC, a smart phone or comparable digital communication devices. In addition, or alternatively, the datasets can comprise vital parameters VP of the patient, in particular blood sugar level, blood pressure, heart rate or suchlike. For this purpose, evaluation device 5 is coupled communicatively V3.2. with diagnostic devices, in particular blood sugar/blood pressure measuring devices or suchlike, and/or computer hardware, in particular fitness trackers. The datasets can be transmitted to evaluation device 5 via the existing coupling of evaluation device 5 with the diagnostic devices, wherein vital parameters VP are essentially taken at the same time as sample 4 with biological material. In addition, or alternatively, the medical information contained in the datasets can at least partially be provided by manual input by the patient, for example into evaluation device 5, into the data-processing device or the diagnostic device.

Alternatively, or in addition, datasets can also contain the patient's drinking and eating behavior, wherein this information can be inputted by manual input by the patient into evaluation device 5 or via a coupling of the latter with a data-processing device, which contains this information.

To this extent, evaluation device 5 can be coupled communicatively not only with one of the mentioned external communication participants 9, i.e., the data-processing device or a diagnostic device, but also with a plurality of external communication participants 9, in particular the data-processing device and the diagnostic devices as well as further external communication participants not explicitly mentioned.

Figure 3:
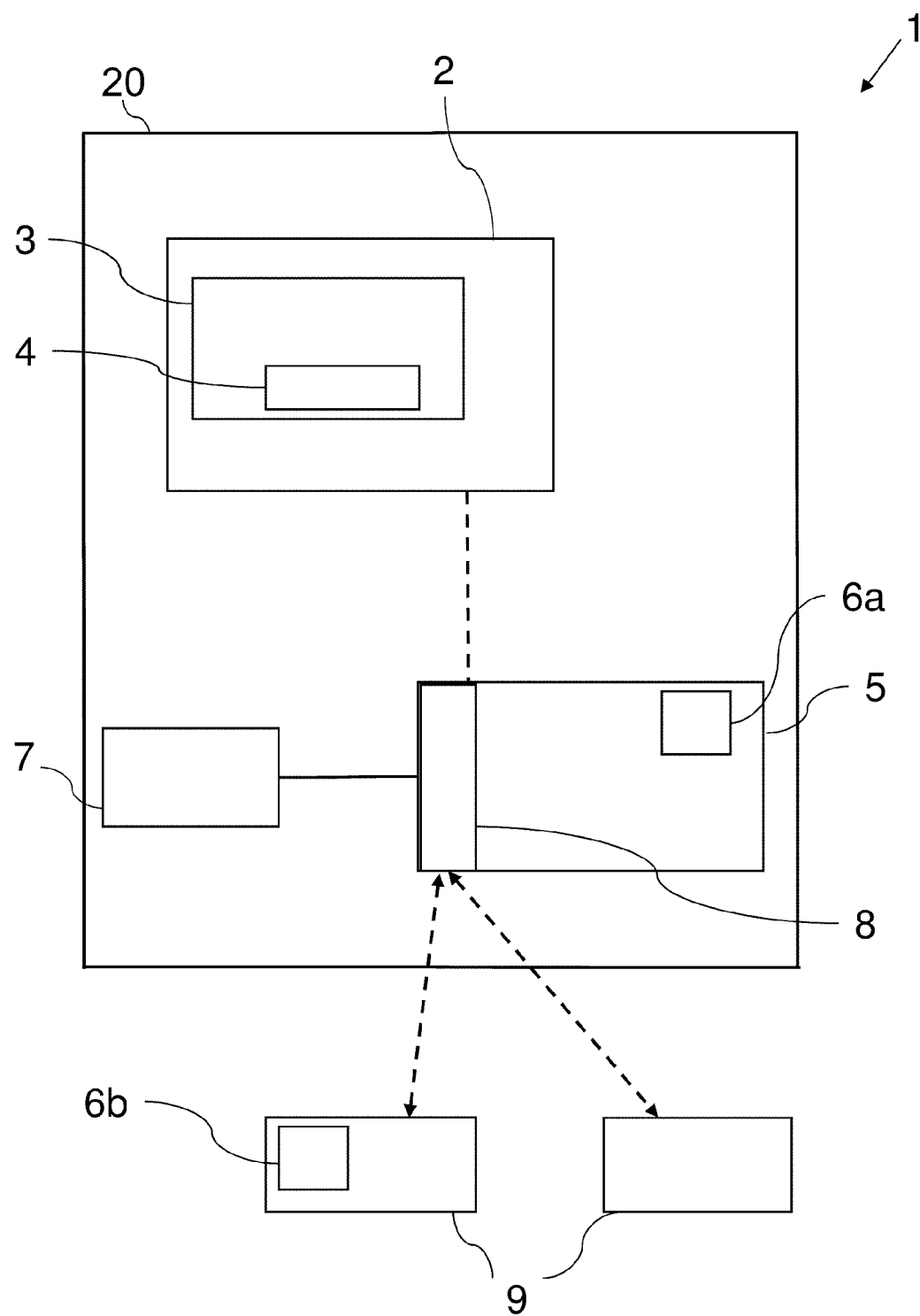
FIG. 3 shows a diagrammatic representation of a system for the analysis, in particular for analysis by dynamic difference calorimetry (DSC), of biological material, in particular blood, urine, sweat or skin tissue, according to an example of embodiment of the invention.

FIG. 3 shows a diagrammatic representation of a system 1 for the analysis, in particular for analysis by dynamic difference calorimetry (DSC), of biological material, in particular blood, urine, sweat or skin tissue of animal or human origin, according to an example of embodiment of the invention. System 1 comprises a measuring device 2, an evaluation device 5 and a display 7.

Measuring device 2 comprises a sensor 3, which contains a sample 4 with biological material of a patient and is designed to send the measured values to evaluation device 5.

For the introduction of sample 4 with biological material into sensor 3, sensor 3 can be constituted such that the biological material can be introduced into measuring device 2 for example by means of a disposable pipette or other handling means. For the automatic acquisition of sample 4 with biological material, in particular blood or sweat, measuring device 2 can comprise openings/channels, through which the biological material can be placed on sensor 3, for example structurally by gravity.

Moreover, measuring device 2 can comprise a power supply (not represented), for example a local energy storage unit, an electronic connection to an energy-carrying device, the energy source whereof is jointly used, or a mains connection. In examples of embodiment carried on the body, the power supply can be provided by the use of thermoelectric generators, which use the waste heat of the body to generate energy.

In a further example of embodiment, measuring device 2 or sensor 3 is a disposable product. For this purpose, measuring device 2 or sensor 3 is preferably designed compatible and interchangeable with other components of system 1, in particular with evaluation device 5.

Evaluation device 5 comprises a first application software instance 6a and is designed to receive measured values and to assess the patient's state of health with the aid of data structures characterizing the state of health on the basis of the measured values. First application software instance 6a can be stored for example as a software program or application on evaluation device 5.

The power supply of evaluation device 5 can correspond to the power supply of measuring device 2. In examples of embodiment in which measuring device 2 is coupled with evaluation device 5 electronically, electrically or in an otherwise energy-transferring manner, a power supply can be provided for measuring device 2 and evaluation device 5.

Furthermore, evaluation device 5 can comprise a communication interface 8, which is designed to establish a communication connection between evaluation device 5 and an external communication participant 9. Moreover, the communication interface is capable of transmitting datasets with medical information from external communication participant 9 to evaluation device 5 for the purpose of assessing the state of health. External communication participant 9 can be constituted at least in three different device categories, wherein the evaluation device is capable of establishing a communication connection to a plurality of external communication participants 9, in particular a plurality of different device categories.

For example, external communication participants 9 can be constituted as a data-processing device, in particular as a server or data memory, for example of a clinic or hospital, and can be coupled communicatively with evaluation device 5 via communication interface 8, wherein the datasets comprise in particular comparable measured values of other patients and/or the treatment measures applied to comparable measured values.

Alternatively, or in addition, external communication participant 9 can be constituted as a diagnostic device, in particular as a blood sugar/blood pressure measuring device or suchlike, and/or as computer hardware, in particular as a fitness tracker. Furthermore, external communication participant 9 can be coupled communicatively with evaluation device 5 via communication interface 8, wherein the datasets preferably comprise vital parameters of the patient, in particular blood sugar level, blood pressure, heart rate and suchlike.

Furthermore, external communication participant 9 can preferably be constituted as a mirror, television, server and/or computer hardware, in particular a PC, smart phone, smart watch and/or fitness tracker, for the visualization or audio-visualization of the state of health.

The coupling of evaluation device 5 with external communication participants 9 for the data transfer via respective communication interfaces 8 can be provided wire-bound, for example USB, LAN, or wireless, for example WLAN or Bluetooth. The coupling of evaluation device 5 with each of external communication participants 9 can be individual and independent the nature of the coupling to other external communication participants 9 and is not limited to one type of coupling between evaluation device 5 and external communication participants 9.

Alternatively, or in addition to first application software instance 6a of evaluation device 5, external communication participant 9 or a server coupled via communication interface 8 can comprise a second application software instance 6b, which enables a more precise assessment of the state of health than first application software instance 6a of evaluation device 5. Application software instances 6a, 6b can be set up, as described in the example of embodiment according to FIG. 1, so that four different application levels for the assessment and visualization of the patient's state of health are possible depending on the medical knowledge to be expected of the user target group.

Furthermore, measuring device 2, evaluation device 5 and display 7 can be at least partially surrounded by a housing 20, in particular a common housing. Furthermore, components of system 1, in particular measuring device 2 and evaluation device 5, can be constituted such that system 1 or components of system 1 are portable, in particular portable on the human body, and/or can be coupled with devices on the body.

Figure 4:
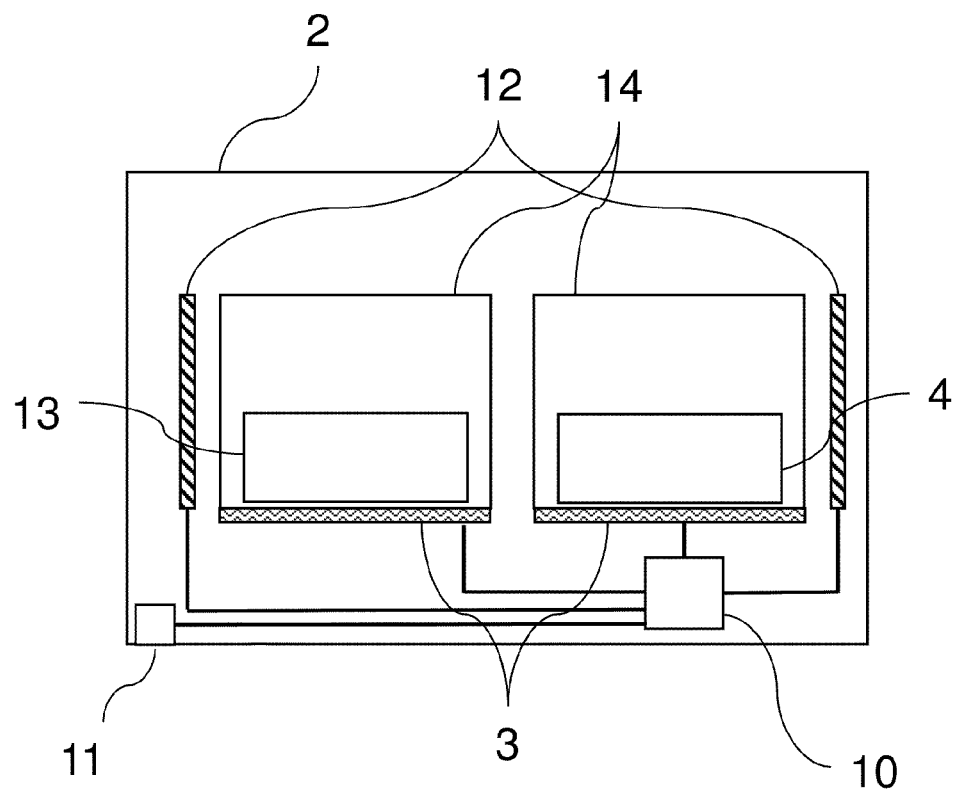
FIG. 4 shows a diagrammatic side view of the measuring device from FIG. 3 according to a further example of embodiment.

FIG. 4 shows a diagrammatic side view of measuring device 2 from FIG. 3 according to a further example of embodiment. This measuring device 2 essentially corresponds to measuring device 2 such as it is described in the example of embodiment according to FIG. 3.

Furthermore, measuring device 2 can be designed to enable a thermal analysis method, in particular a dynamic difference calorimetry (DSC), for the measurement of a released or absorbed amount of heat of the biological material during a thermal process. Measuring device 2 can comprise for example temperature-control elements 12, by means of which sample 4 and a reference 13 can be heated and/or cooled, for example from −50° C. to approximately 250° C., preferably from room temperature to approximately 100° C.

Moreover, the measuring device according to FIG. 4 can comprise a control 10 and a communication interface 11, wherein control 10 is electronically connected to at least one of the components of measuring device 2. By means of control 10, temperature-control elements 12 for example can be controlled according to the thermal analysis method used and/or the communication with evaluation device 5 via communication interface 11.

In the preceding detailed description, various features for improving the stringency of the representation have been summarized in one or more examples. It should however be clear that the above description is only illustrative, but under no circumstances of a limiting nature. It serves to cover all the alternatives, modifications and equivalents of the various features and examples of embodiment. Many other examples will be immediately and directly clear to the specialist on account of his specialist knowledge in view of the above description.

The examples of embodiment have been selected and described in order to be able to represent in the best possible way the principles underlying the invention and the possible applications in practice. Specialists can thus modify and use the invention and its various examples of embodiment in the optimum manner in respect of the intended use. In the claims and the description, the terms "containing" and "comprising" are used as linguistically neutral terminology for the corresponding term "including". Furthermore, a use of the term "a/an" is not in principle intended to eliminate a plurality of features and components thus described.

The invention claimed is:

1. A method analyzing a biological material, comprising:
introducing a sample with a patient's biological material onto a sensor of a measuring device;
acquiring measured values of the sample by means of the measuring device;
sending the measured values to an evaluation device, which communicates with the measuring device;
sending datasets with medical information from an external communication participant to the evaluation device;
assessing, via a first application software instance performed on the evaluation device, the patient's state of health with the aid of data structures characterizing the state of health on the basis of the measured values and the datasets, wherein the external communication participant include a second application software instance which is designed to send the datasets to the evaluation device and provide a more precise assessment of the state of health than the first application software instance of the evaluation device; and
visualizing or audio-visualizing the state of health on a display.

2. The method according to claim 1, wherein the measuring device performs a thermal analysis process for measuring a released or absorbed amount of heat of the biological material during a thermal process.

3. The method according to claim 1, wherein the measuring device or the sensor is disposed of after the step of assesing the patient's state of health.

4. A method of analyzing a biological material, comprising:
introducing a sample with a patient's biological material onto a sensor of a measuring device;
acquiring measured values of the sample by means of the measuring to device,
sending the measured values to an evaluation device, which communicates with the measuring device;
assessing, via a first application software instance performed on the evaluation device, the patient's state of health with the aid of data structures characterizing the state o health on the basis of the measured values; and
visualizing or audio-visualizing the state of health on a display;
wherein datasets with medical information are considered in the addition to the measured values in said step of assessing the patient's state of health;
wherein the datasets comprise comparable measured values of other patients and the datasets are transmitted to the evaluation device by communicative coupling of the evaluation device with a data-processing device.

5. The method according to claim 1, wherein the evaluation device communicates with the external communication participant via a communication interaface, wherein the external communication participant comprises a mirror, a television a PC, a smart phone, a smart watch, and/or a fitness tracker.

6. The method according to claim 5, wherein the external communication participant is a device or a server, and
wherein the second application software instance stored on the device or on the server is performed during the assessment of the state of health and/or the state of health is visualized or audio-visualized on a display of the device.

7. The method according to claim 1, wherein the method further comprises a step of controlling a communication-enabled installation in the a building in order to support treatment measures for the patient depending on the assessed state of health.

8. The method according to claim 7, wherein the communication-enabled installation comprises a heating system, a ventilation system, and/or an alarm in the building.

9. The method according to claim 7, wherein the step of controlling comprises adapting a room temperature, air humidity, and/or brightness of surroundings of the patient according to the treatment measures for the patient.

10. The method according to claim 7, further comprising transmitting visually and/or acoustically to the patient upcoming medication times or other reminders.

11. The method according to claim 4, wherein the datasets comprise treatment measures applied to the comparable measured values.

12. The method according to claim 4, wherein the datasets comprise vital parameters of the patient, which are transmitted to the evaluation device by communicative coupling of the evaluation device with diagnostic devices and/or computer hardware, wherein the vital parameters are taken essentially at the same time as the sample is taken.

13. The method according to claim 4, wherein the measuring device performs a thermal analysis process for measuring a released or absorbed amount of heat of the biological material during a thermal process.

14. The method according to claim 4, wherein the measuring device or the sensor is disposed of after the step of assessing the patient's state of health.

15. The method according to claim 4, wherein the evaluation device communicates with a device via a communication interface, wherein the comprises a mirror, a television, a PO, a smart phone, a smart watch, and/or a fitness tracker.

16. The method according to claim 4, wherein the method further comprises a step of controlling a communication-enabled installation in a building in order to support treatment measures for the patient depending on the assessed state of health, wherein the communications-enabled installation heating system a ventilation system, and/or an alarm.

17. A method of analyzing a biological material, comprising:
   introducing a sample with a patient's biological material onto a sensor of a measuring device;
   acquiring measured values of the sample by means of the measuring device;
   sending the measured values to an evaluation device, which communicates with the measuring device;
   assessing, via a first application software instance performed on the evaluation device, the patient's state of health with the aid of data structures characterizing the state of health on the basis of the measured values; and
   visualizing or audio-visualizing the state of health on a display;
   wherein datasets with medical information are considered in addition to the measured values in said step of assessing the patient's state o health;
   wherein the datasets comprise vital parameters of the patient, which are transmitted to the evaluation device by communicative coupling of the evaluation device with diagnostic devices and/or computer hardware, wherein the vital parameters are taken essentially at the same time as the sample is taken.

18. The method according to claim 17, wherein the vital parameters comprise blood sugar level, blood pressure, and/or heart rate.

19. The method according to claim 17, wherein the diagnostic devices comprise a blood sugar measuring device, a blood pressure measuring device, and/or a heart rate measuring device.

20. The method according to claim 17, wherein the computer hardware comprises a fitness tracker.

* * * * *